United States Patent [19]

Vantard

[11] Patent Number: 4,617,115
[45] Date of Patent: Oct. 14, 1986

[54] ARTIFICIAL KIDNEY WITH DISPOSABLE DIALYSIS LIQUID CIRCUIT

[75] Inventor: Georges Vantard, Gournay-sur-Marne, France

[73] Assignee: Hospal Industrie, Meyzieu, France

[21] Appl. No.: 517,805

[22] Filed: Jul. 27, 1983

Related U.S. Application Data

[63] Continuation of Ser. No. 293,464, Aug. 17, 1981, abandoned.

[30] Foreign Application Priority Data

Oct. 6, 1980 [FR] France ............................. 80 21781

[51] Int. Cl.⁴ ........................................... B01D 13/00
[52] U.S. Cl. .................................... 210/90; 210/96.2; 210/321.3
[58] Field of Search ............... 210/321.1, 321.2, 321.3, 210/89, 90, 96.2, 85

[56] References Cited

U.S. PATENT DOCUMENTS

| | | | |
|---|---|---|---|
| 3,608,729 | 9/1971 | Haselden | 210/321.3 |
| 4,079,007 | 3/1978 | Hutchisson | 210/85 |
| 4,132,644 | 1/1979 | Kolberg | 210/85 |
| 4,231,871 | 11/1980 | Lipps et al. | 210/321.3 X |
| 4,269,708 | 5/1981 | Bonomini et al. | 210/90 |
| 4,370,983 | 2/1983 | Lichtenstein | 210/321.2 X |

Primary Examiner—Frank Spear
Attorney, Agent, or Firm—Gerald D. Sharkin; Robert S. Honor; Walter F. Jewell

[57] ABSTRACT

An artificial kidney comprising a haemodialyser connected to a dialysis liquid circuit has the dialysis liquid circuit designed and simplified so as to be entirely disposable. Preferably, the haemodialyser and also all the circuits for the blood, for the dialysis liquid and for removing the ultrafiltrate are disposable. They can be delivered in a disposable container which can, during treatment, be used as a support and as a dialysis liquid reservoir. A small console includes the re-usable means for controlling and checking the artificial kidney, together with their electric circuits.

8 Claims, 6 Drawing Figures

ARTIFICIAL KIDNEY WITH DISPOSABLE DIALYSIS LIQUID CIRCUIT

This is a continuation of application Ser. No. 293,464, filed Aug. 17, 1981, now abandoned.

DESCRIPTION

1. Background to the Invention

The present invention relates to an artificial kidney, and more particularly to an artificial kidney of an improved and simplified type in which the elements constituting the hydraulic circuit through which the dialysis liquid passes are designed, manufactured and assembled as disposable items.

An artificial kidney generally comprises:

(a) a haemodialyser divided up into two compartments by a membrane making it possible to treat the blood by dialysis and by ultrafiltration, the blood passing through the first compartment and the dialysis liquid passing through the second compartment, (b) means for causing the treated blood to circulate in the first compartment, (c) means for preparing the dialysis liquid, storing it and causing it to circulate in the second compartment, (d) means for removing and measuring amounts of liquid equal to the desired amounts of ultrafiltrate, and (e) members for controlling and checking the said means of (b) and (c).

For obvious safety reasons, the means (a) and (b), which consist of elements through which the blood circulates, are not generally re-used. They are therefore designed as disposable items, and it has already been proposed to combine them in a disposable unit in order to reduce their cost and to simplify their use.

In contrast, the means of (c) and (d) can generally only be re-used after sterilisation. Therefore, they most frequently form part of an apparatus referred to as a monitor, which is designed for repeated use, many times over, and which also groups together the various electrically connected members of (e) for the control, checking and safety of the treatment. It is well known that the manufacture of the means of (c) and (d) is very expensive and that their operation requires qualified staff.

2. Prior Art

Admittedly, many attempts have been made to dispense with any prior sterilisation treatment, by using disposable lines for the dialysis liquid. However, the only result has been that tubing capable of repeated re-use in the known types of apparatus has been replaced by disposable tubing, whilst the other existing members have been retained.

BRIEF SUMMARY OF THE INVENTION

One object of the present invention is to provide an artificial kidney of a new, improved and simplified type in which, in particular, the means for preparing the dialysis liquid, for storing it and for causing it to circulate are disposable.

Another object of the present invention is to provide an artificial kidney in which the majority of the elements are suitable for economical mass-production.

Another object of the present invention is very substantially to reduce the cost of the immobilisation of the haemodialysis equipment which can be re-used after each treatment.

Another object of the present invention is to speed up and to simplify the use of an artificial kidney very substantially, whilst at the same time increasing the safety in use, thus permitting the development of dialysis in the home.

Another object of the present invention is substantially to reduce the overall cost of a haemodialysis session, thus permitting an expansion of the haemodialysis market.

Accordingly, the present invention provides, in an artificial kidney comprising:

(a) a haemodialyser divided up into first and second compartments by a membrane making it possible to treat blood by dialysis and by ultrafiltration whereby the blood passes through the first compartment and the dialysis liquid passes through the second compartment, (b) hydraulic circuit means for causing the treated blood to flow in the first compartment, (c) hydraulic circuit means for preparing the dialysis liquid, storing it and causing it to flow in the second compartment, (d) hydraulic circuit means for removing and measuring amounts of liquid equal to the desired amounts of ultrafiltrate, and (e) means for controlling and checking the said means (b) and (c), said controlling and checking means being re-usable and grouped together on a console capable of being connected to an electricity supply, the improvement wherein at least one of said dialysis liquid hydraulic circuit means (c) and said liquid removing and measuring hydraulic circuit means (d) is designed, manufactured and assembled as disposable items, and said console is isolated from said disposable hydraulic circuit means.

According to one characteristic of the present invention, the means for preparing the dialysis liquid, for storing it and for causing it to circulate can be disposable as a result of substantial simplifications which most frequently entail dispensing with certain components.

Thus, in contrast to the usual methods, it has been found possible and advantageous to deliver the dialysis liquid into the haemodialyser at a pressure which is, by virtue of a suitable automatic regulation device, maintained at slightly above atmospheric pressure, although remaining constantly below the blood pressure; this makes it possible to dispense with manometers and to avoid or considerably to reduce the problems of degassing and the risks of re-entry of air.

Moreover, the dialysis liquid and the ultrafiltrate withdrawn from the patient are displaced by volumetric methods, which makes it possible to dispense with all weighing of liquid, or of the patient, or of all or part of the apparatus. Likewise, the use of a predetermined volume of dialysis liquid prepared beforehand makes it possible to dispense with means for continuous measurement of the conductivity of this liquid, without incurring any consequent risk to the safety of the patient.

Furthermore, as a result of dispensing with all sterilisation, the sterilisation operations themselves, and also the risks inherent in this technique, disappear together with the means and the arrangements connected with the use of sterilisation.

According to another characteristic of the present invention, all the disposable elements required for a haemodialysis session, including in particular the means for preparing the dialysis liquid, for storing it, and for ensuring its circulation, have a capacity which preferably corresponds precisely to the total volume of dialysis liquid required for a session, that is to say only about thirty liters.

This exhibits the advantage of arranging all the disposable elements required for a haemodialysis session in a container which cannot be deformed under the effect of the usual stresses and which can be used for multiple purposes, and this preferably makes it possible to manufacture it as a disposable item.

In fact, this container makes it possible to contain, to transport, to store and to deliver, before and/or after a dialysis session, all the disposable elements required for such a session. Furthermore, during the session, the container delimits and contains, without substantial deformation, the exact volume of fresh and/or used dialysis liquid required for the treatment. Preferably, during the session, the container keeps the dialysis liquid at temperatures similar to the blood temperature. Moreover, during the session, the container can advantageously serve as a support for all the equipment constituting the artificial kidney.

After each session, the disposable equipment can then either be thrown away immediately or be put back into the container; it is furthermore possible for the unit thus formed to be either thrown away or exchanged for an identical new unit, which considerably reduces the handling operations and the risks of error, losses or damage. If appropriate, the container can be returned to the workshop, treated, tested and recycled.

Indeed, use has been made of the fact that treatments can advantageously be carried out with relatively moderate purification levels defined, for example, by a weekly clearance of 70 to 90 liters of urea and 20 to 30 liters of vitamin B12. Such treatments are possible, in particular, with haemodialysers having a surface area reduced to 0.5 m$^2$, which are equipped with membranes such as those described in U.S. Pat. Nos. 4,545,910 and 3,930,105. Consequently, with an artificial kidney according to the present invention, it is possible to reduce the total volume of dialysis liquid from about 200 to 300 liters to a volume of less than about 80 liters.

The volume of dialysis liquid can moreover be further reduced and can be adjusted to values of about 30 liters, either by carrying out a partial purification of the recycled dialysis liquid by passing it over adsorbent products such as activated charcoal, or by operating at a low flow rate of dialysis liquid, without recirculating or mixing the used liquid with the fresh liquid, as will be described below.

According to another characteristic of the present invention, the artificial kidney is entirely composed of (a) disposable elements, with the exception of a small console which is arranged at the top part and only groups together means for controlling and checking the artificial kidney, and also (b) the corresponding electric circuits capable of being connected to an external electricity supply by means of a lead.

It is noted that this console is devoid of any hydraulic circuit, in particular the circuit for preparing or circulating the dialysis liquid and also for removing and checking amounts of liquid equal to the desired amounts of ultrafiltrate; this is an important characteristic of the present invention. The fact that the electric circuits of the console are no longer mixed with hydraulic circuits constitutes a very great improvement in the operational safety of the artificial kidney.

It is also apparent from this fact that the size of the console, which is virtually the only element of the artificial kidney to be re-used from one treatment to the next, is minimal, that it is also easy to handle and that the purchase price is considerably reduced.

Furthermore, but in a conventional manner, the disposable elements are generally delivered to the user before each session, already in assembled, checked and sterilised condition, in a sealed pack and ready to use.

BRIEF DESCRIPTION OF THE DRAWINGS

Other objects and advantages of the present invention will become apparent in the course of the following description given with reference to the accompanying figures, which show various embodiments, schematically and with no fixed scale. In the drawings.

DESCRIPTION OF THE PREFERRED EMBODIMENTS

Figure 3:
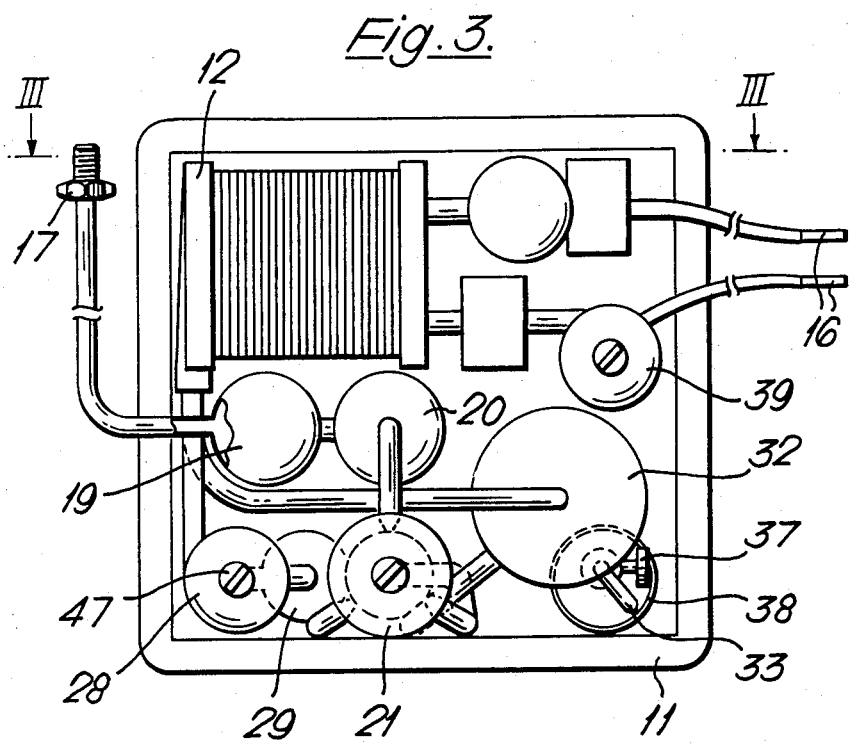
FIG. 3 is a top plan view of the elements of FIG. 2.

Referring now to the drawings, and in particular to FIG. 3, it will be seen that all the disposable equipment is arranged in four zones delimited approximately by the planes of symmetry of the container 11. In fact, starting in the top left-hand corner and then working successively in a clockwise direction round the drawing, this Figure shows:

the haemodialyser 12, the means constituting the blood circuit connecting the haemodialyser to the patient via the blood pump 39 and the cannulae 16 the means 37,38 for removing and checking amounts of dialysis liquid equal to the desired amounts of ultrafiltrate, and finally the means for preparing and circulating the dialysis liquid.

Figure 1:
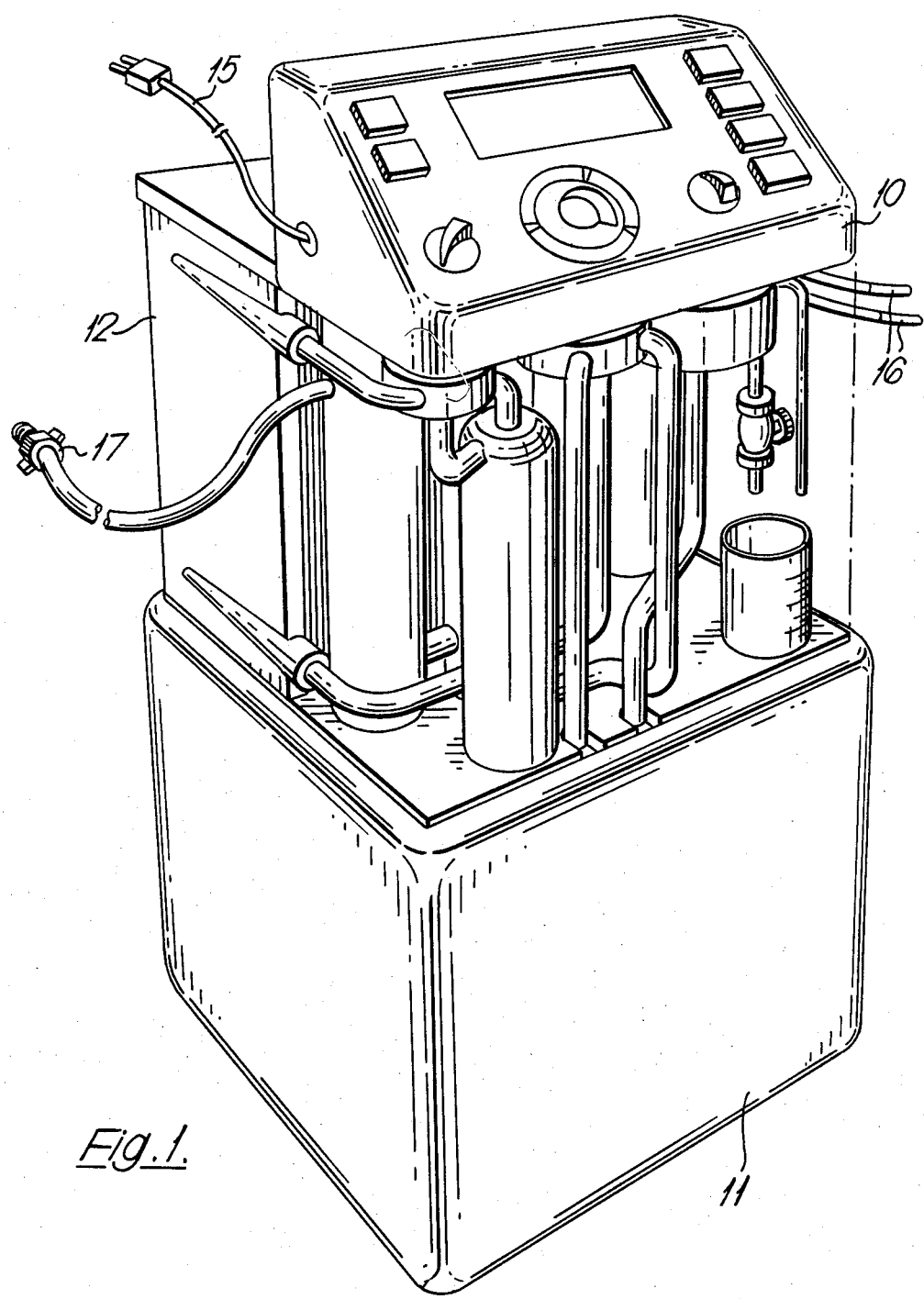
FIG. 1 is a perspective view of one particular embodiment of the whole artificial kidney according to the invention.
Figure 2:
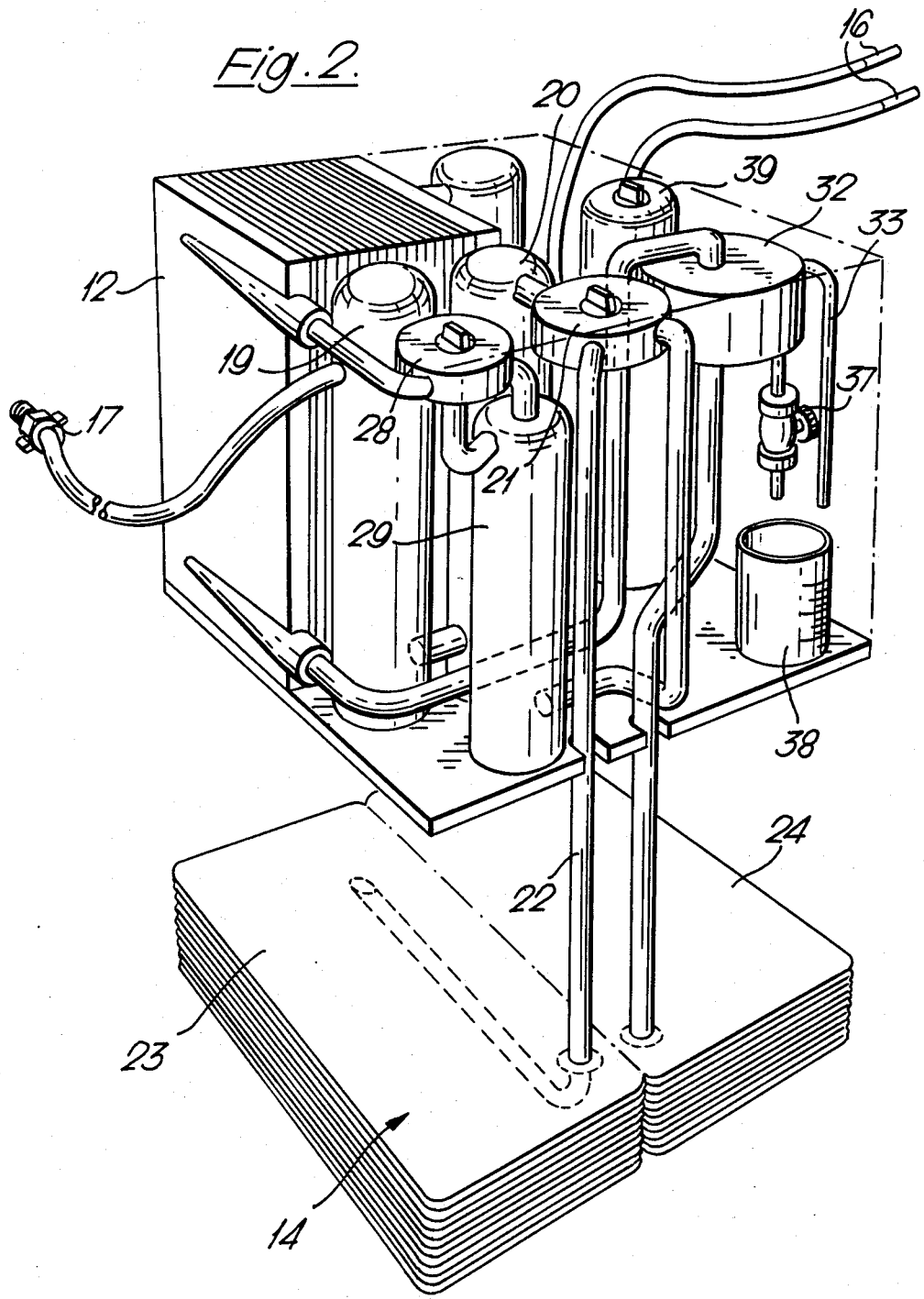
FIG. 2 is a perspective view of the disposable elements connected to the haemodialyser of an artificial kidney similar to the one shown in FIG. 1.

All these means appear in FIG. 1 between the console 10 at the top and the container 11 at the bottom. FIG. 2 also shows an air-free leaktight flexible bag 14 folded back on itself (i.e. concertina-folded), intended for containing the exact volume of dialysis liquid required.

Figure 4:
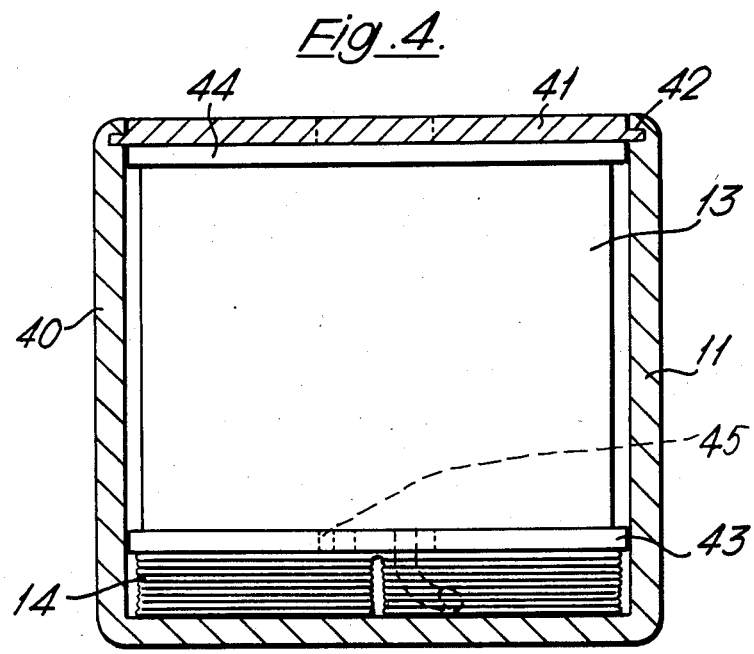
FIG. 4 is a view, in section along line III—III of FIG. 3, of all the disposable elements.
Figure 6:
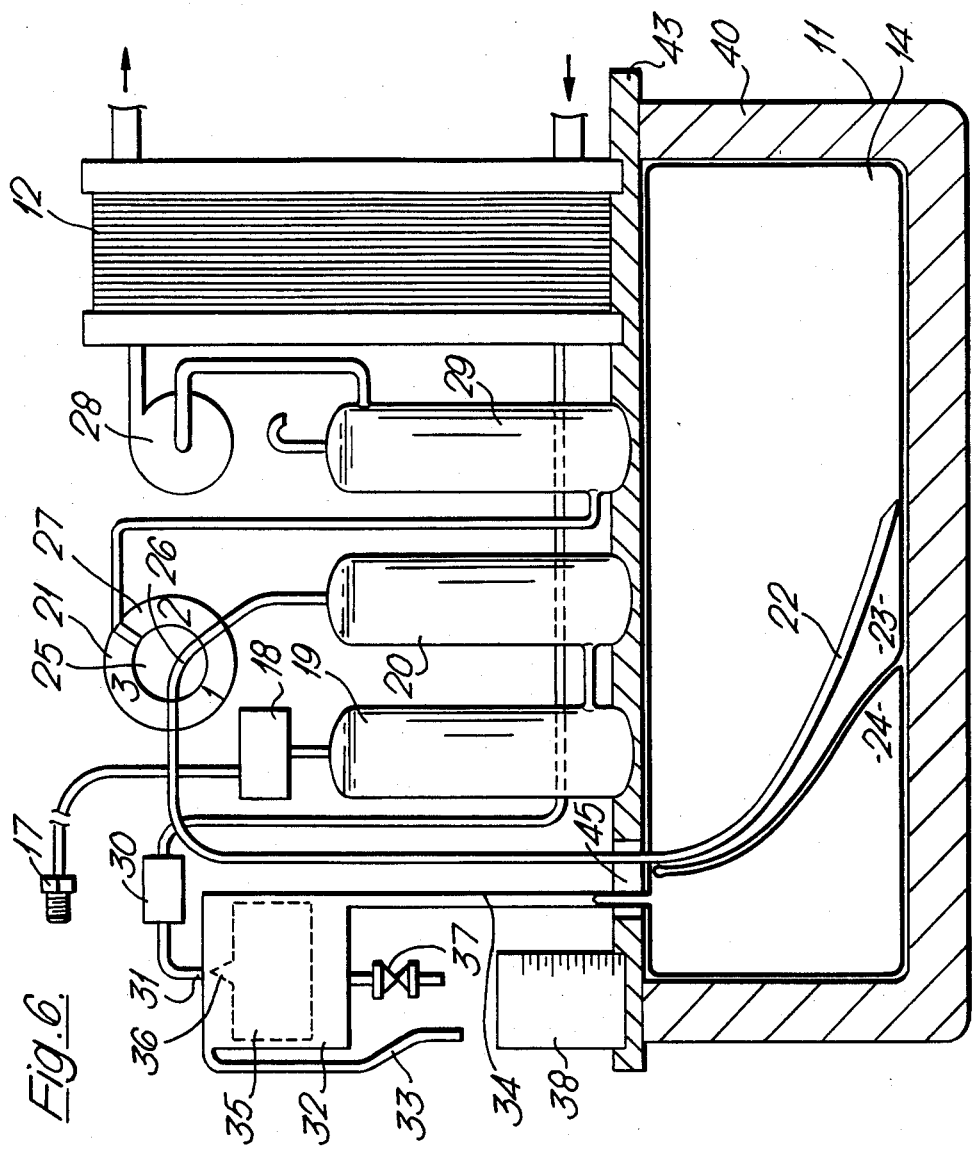
FIG. 6 is a flow diagram for the dialysis liquid in a particular embodiment of the artificial kidney of the present invention.

FIG. 4 shows a particular embodiment of a container 11 comprising a tank 40 and a cover 41 which slides in two parallel grooves such as 42. The disposable equipment shown schematically by the rectangle 13, and also the storage bag 14, are located inside the container. Two parallel plates 43 and 44 serve to keep the various disposable elements assembled and in position. These disposable plates can be rendered integral by any means, for example by a connecting rod (not shown) screwed to their respective centres. The lower plate 43 is provided with an opening 45 which allows the tubes 22 and 34 to pass therethrough. The various disposable elements can be rendered integral with these plates, as is indicated in FIG. 6 for the lower plate 43.

Figure 5:
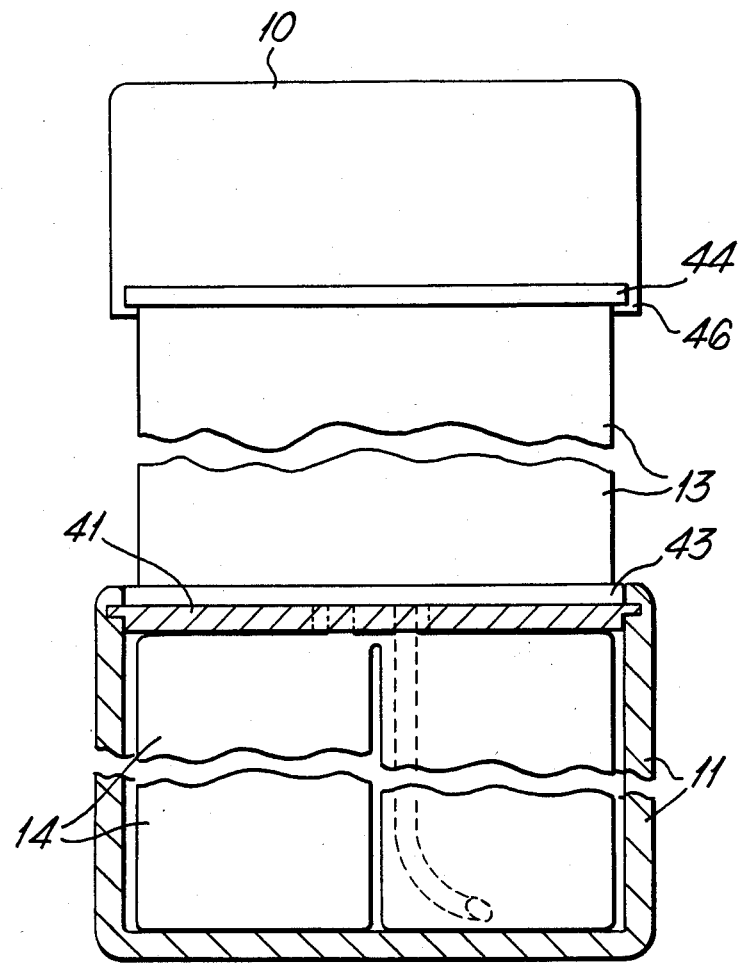
FIG. 5 is a view in section, along line III—III of FIG. 3, of the whole artificial kidney of FIG. 1, ready for operation.

In FIG. 5, the cover 41 has been removed to enable the disposable equipment to be taken out of the container 11. The cover 41 has then been put back in its grooves after having been turned over, in order to make it possible for the disposable equipment to be placed on the top of the container and for the lower plate 43 to be able to fit exactly inside the container, on the cover 41.

The console 10 is advantageously provided with two lateral grooves such as 46 (FIG. 5), which co-operate with the corresponding edges of the upper plate 44. The console 10 is thus mounted on the plate 44 by translational movement, until the various mechanical coupling members, corresponding, for example, to the disposable pumps and valves on the one hand, and to their re-usable driving means (motors, flywheels) on the other hand, engage, for example with the aid of square bit drives fitting into corresponding female devices. It then remains merely to make the necessary electric connections and to test that all the connections have been made correctly.

The haemodialyser is divided up, by a membrane permitting the dialysis and ultrafiltration of the blood, into a first compartment through which the blood flows and a second compartment through which the dialysis liquid flows, preferably in counter-current direction. The haemodialyser can be of various known types and the areas of the exchange surfaces can have any of the customary values. A hollow-fibre haemodialyser is suitable, but haemodialysers with a membrane which is of planar general shape or is folded around solid or perforated plane spacers are preferred, because their rather precise geometry favours exchange with a low flow rate of dialysis liquid (low-flow) and degassing can be carried out without turning the apparatus over.

The disposable means constituting the circuit through which the blood flows and connecting the haemodialyser to the patient are also of any known type and will not therefore be described in greater detail.

One embodiment of the means for preparing and storing the dialysis liquid and for causing it to circulate and also for checking the ultrafiltrate to be removed from the patient, is shown schematically in FIG. 6.

This disposable circuit can be connected by means of an adaptor 17 to any supply of running water. This water can be supplied either at ambient temperature or, preferably, at a temperature between approximately 35° C. and 40° C. via the prior thermostatically-controlled mixing of cold water and hot water.

The disposable circuit advantageously possesses a transparent window 18 making it possible to check the flow of the water introduced. If appropriate, this window can be provided with a calibrated clack valve which automatically limits the pressure of the water in the disposable circuit.

This circuit can also possess a disposable water softening device 19 provided, for example, with ion exchange resins of types which are in themselves known, or with reverse osmosis membranes on cords, as disclosed in French Patent Specification No. 74/23,310.

Next, it possesses a disposable reservoir 20 containing a cartridge of dialysis concentrate in the form of a powder or, preferably, in the form of a concentrated solution; the total amount (weight or volume) of the concentrate is calibrated beforehand so as to correspond exactly to the capacity of the circiut. About one liter of a concentrated solution is required in order to prepare 30 liters of dialysis liquid; the volume of the concentrated solution must be defined with a precision of ±25 ml.

This concentrate can be contained, for example, in a plastic bag which is sealed in a leaktight manner and which is provided with a calibrated clack valve integral with an axial punch capable of perforating the opposite wall of the bag. Under the effect of the pressure of the water, the clack valve is displaced and the punch perforates the bag, thereby simultaneously effecting the introduction of the water into the bag and the discharge of the mixture of water and concentrate downstream of the bag.

This mixture is then sent, via a 3-way tap 21 and a dip tube 22, to the bottom of the container 11 until the latter has been entirely filled.

It has been found that, when the water/dialysis concentrate mixture is sent to the bottom of the container, the mixture rapidly becomes homogeneous under the effect of convection currents without mechanical intervention. It also becomes superfluous to provide a conductivity meter for measuring, checking or adjusting the conductivity of the mixture, and this in total constitutes a substantial saving.

According to a particular embodiment the container 11, provided with walls which cannot be deformed under the usual stresses, can, as shown, contain a disposable flexible bag 14 which is leaktight to fluids. This flexible bag can be divided into two complementary compartments 23 and 24 in such a way that each compartment is capable of occupying the whole of the available internal volume. One of these compartments 23 can receive and contain the fresh dialysis liquid, and the other 24 the used dialysis liquid.

The three-way tap 21 advantageously consists of a cylindrical rotor 25 provided with a channel 26 which is capable of rotating in a leaktight manner inside a body 27 provided with three radial orifices which are preferably 120° apart, in order to be able to bring any two of these three orifices into communication. FIG. 6 shows this tap in position '1', that is to say the position which connects the two orifices located on either side of the reference numeral '1'.

Thus, when the compartment 23 is full, that is to say when it can be observed through the window 18 that the water has ceased to flow, the tap 21 is rotated by a third of a turn in order to move it from position '1' to position '2'. The dialysis liquid circuit comprising the haemodialyser, downstream of the three-way tap, is initially filled with water, virtually without consuming any dialysis concentrate. The tap is generally controlled from the console 10 by virtue of a driving device which is mechanically coupled to the rotor 25 during the positioning of the console.

The water then flows through the pump 28 and the haemodialyser 12. If appropriate, the water passes through a conventional device 29 for heating by circulating hot water from the water supply tap, or by an infra-red heater. This device 29 is complemented by a temperature-regulating device, the electrical devices being integral with the console 10 and not being in contact with the liquids. The device 29 can optionally possess a degassing device.

The pump 28 is of conventional type, for example a peristaltic pump, a centrifugal pump, a gear pump, or the like. It is caused to rotate by means of a shaft 47 which is capable of being coupled to the shaft of an electric drive motor housed in the console 10. Most frequently, a similar motor, also housed in the console 10, drives, via a suitable coupling, the pump 39 which moves the blood from the patient into the haemodialyser.

On leaving the haemodialyser, the dialysis liquid passes through a transparent tube element 30 co-operating with a colorimeter of a type which is in itself known, housed in the console 10.

Via the orifice 31, the dialysis liquid then enters the upper part of a tank 32 which is open to the atmosphere through a tube 33 and which has its bottom connected in a leaktight manner, via a tube 34, to the compartment 24 of the bag 14 located in the container 11. Inside the tank a float 35, the top of which is provided with a conical needle-valve 36, co-operates with the orifice 31 to form a shut-off device. This float-type shut-off device automatically regulates the pressure of the dialysis liquid in the haemodialyser. A tap 37 is connected to the bottom of the tank 32, and a graduated receiver 38 is arranged under the tap 37 and the tube 33. With the tap 37 closed, and with the compartment 24 initially devoid of air and offering no available volume, the liquid enters the tank 32 until the float rises to shut off the orifice 31. The circuit of the dialysis liquid is then full.

Advantageously, the compartments of the haemodialyser through which the blood and the dialysis liquid are intended to pass are simultaneously rinsed. The compartment intended for the blood is rinsed in a conventional manner and is then connected to the patient.

To rinse the compartment intended for the dialysis liquid, the three-way tap is rotated by a further one-third of a turn in order to move it from position '2' to position '3', and the pump 28 is started and moves the water towards the complementary compartment 24 and replaces it by the dialysis liquid originating from the bottom of the compartment 23 in the container 11. After a few moments, as soon as the fresh dialysis liquid has filled the corresponding compartment of the haemodialyser and the patient has been simultaneously connected to the haemodialyser, the artificial kidney according to the invention is ready to operate.

The three-way tap remains in position '3' and the pump 28 causes the fresh dialysis liquid to circulate at the desired rate. The used dialysis liquid progressively enters the compartment 24 and displaces an equal volume of fresh liquid from the complementary compartment 23 of the bag 14 inside the container 11.

Any volume of dialysis liquid collected in the graduated receiver 38 by opening the tap 37 is progressively replaced by an equal volume of ultrafiltrate passing through the membrane of the haemodialyser, so that the volume of the dialysis liquid in the disposable circuit remains constant. The haemodialysis and ultrafiltration of the blood are carried out in this way, as desired. The session ends when the total amount of fresh dialysis liquid has been used and displaced from the container 11 by an equal volume of used dialysis liquid, by means of the pump 28, through the haemodialyser 12. Simultaneously, an amount of dialysis liquid equal to the desired amount of ultrafiltrate has been removed from the graduated receiver 38, at the desired rate and with the desired frequency.

In general, the liquid accumulated in the compartment 24 of bag 14 is emptied down the drain. To do this, it is possible, for example, to rotate the tap 21 by a further third of a turn in order to move it back to position '1' and to connect the adaptor 17 to a device (not shown) capable of supplying air under a pressure of a few decimeters of water. This device can consist of a bag having a clack valve of a commercially available type which can be hand-operated or foot-operated. The tap 37, the adaptor of which will have been provided beforehand with a flexible tube (not shown) connected to the drain, is then opened. Under the effect of the air pressure exerted in the compartment 23 the used dialysis liquid contained in the compartment 24 rises back into the tank 32 and flows to the drain through the valve 37 preferably by syphoning. It is also possible simply to start the syphon with the aid of the dialysis liquid collected in the graduated receiver 38.

The disposable equipment can then be put back in the container 11 to be exchanged for a new identical unit.

The disposable elements of the artificial kidney according to the present invention essentially consist of rigid reservoirs, flexible bags and elements of tubing having shapes which are simple to manufacture. They are advantageously made of inexpensive thermoplastics, processed in accordance with known techniques of compression-moulding, injection-moulding and cutting, permitting mass production at low cost. Moreover, they are assembled and checked beforehand at the place of manufacture, which very substantially reduces the risks of error when brought into service.

Advantageously, the flexible bag 14 consists of a film or a sleeve sealed at the edges, which is made of a virtually unstretchable material such as extruded polyethylene. The container 11 is preferably constructed from a thermally-insulating material such as expanded polystyrene or expanded polyethylene, so as to keep the dialysis liquid, as far as possible, at a temperature close to the temperature of use.

Of course, the artificial kidney according to the present invention can be subject to a large number of modifications by those skilled in the art, without departing from the scope of the present invention as defined by the following claims.

The saving in terms of products, fluids or heat, to be used for each session, may be emphasised again as advantages of the artificial kidney according to the invention. Thus, by comparison with a conventional artificial kidney, the volume of water consumed is reduced by a factor of 5, and hence the consumption of heat energy and water softener and of dialysis concentrate are also reduced by a factor of 5. Furthermore, the consumption of sterilising liquids is totally eliminated.

Moreover, a fact which is greatly appreciated by users and in particular patients at home, the time required to prepare and put away the equiment in each session is reduced.

Thus, for a haemodialysis session lasting 4 hours, with a conventional artificial kidney it is necessary to add 2 hours for preparing and putting away the equipment, this time being considerably reduced with the kidney according to the invention. This enables the patient who starts his treatment at home, three times weekly at 6 pm, to finish it well before midnight.

I claim:
1. In an artificial kidney comprising:
   (a) a haemodialyser divided up into first and second compartments by a membrane making it possible to treat blood by dialysis and by ultrafiltration whereby the blood passes through the first compartment and the dialysis liquid passes through the second compartment,
   (b) hydraulic circuit means for causing the treated blood to flow in the first compartment,

(c) hydraulic circuit means for preparing the dialysis liquid, storing it and causing it to flow in the second compartment, (d) hydraulic circuit means for removing and measuring amounts of liquid equal to the desired amounts of ultrafiltrate, and (e) means for controlling and checking the means (b) and (c), the controling and checking means being re-usable and grouped together on a console capable of being connected to an electricity supply, the improvement wherein the circulation pump corresponding to said hydraulic circuit means (c) is disposed upstream of the dialyzer and an automatic regulation device maintains at any time within the dialyzer the pressure of the dialysis liquid between the atmospheric pressure and the blood pressure, and furthermore wherein the dialysis liquid hydraulic circuit means (c) and the liquid removing and measuring hydraulic circuit means (d) are designed, manufactured and assembled as a disposable items.

2. An artificial kidney according to claim 1, wherein said dialysis liquid preparation and storage hydraulic circuit means (c) comprise a disposable cartridge of a calibrated total amount of dialysis concentrate, and said disposable cartridge is capable of being connected to a supply of running water.

3. An artificial kidney according to claim 1, wherein said disposable dialysis liquid hydraulic circuit means and said liquid removing and measuring hydraulic circuit means are connected to the haemodialyser beforehand and forms, with the latter, a sterile unit in a leak-tight pack and ready to use.

4. An artificial kidney according to claim 3, wherein said sterile unit required for a haemodialysis session can be positioned and delivered inside a container which is intended to contain, without substantial deformation, the volume of dialysis liquid required for a treatment.

5. An artificial kidney according to claim 3, wherein the container is constructed from a thermally-insulating material.

6. An artificial kidney according to claim 1, wherein said dialysis preparation and storage hydraulic circuit means (c) comprise a 3-way tap capable of connecting, in pairs, in three different combinations, a liquid mixture introducing tube capable of supplying the dialysis liquid, a zone for storing dialysis liquid, and a pump for circulating the said dialysis liquid.

7. An artificial kidney according to claim 1, wherein said dialysis preparation and storage hydraulic circuit means (c) comprise, downstream of the said second compartment of the haemodialyser: a tank open to the atmosphere, said tank being provided with a float, means capable of shutoff control of the tube connecting it to the outlet orifice for the dialysis liquid in the direction of the haemodialyser: and a tube connecting the bottom of the tank to the container.

8. An artificial kidney according to claim 7, wherein said liquid removing and measuring hydraulic circuit means comprise means for removing the liquid contained in said tank, and means for measuring the volume of the liquid removed in this way.

* * * * *